United States Patent [19]
Lehle

[11] Patent Number: 4,563,634
[45] Date of Patent: Jan. 7, 1986

[54] MEASURING AND LINEARIZING CIRCUIT DEVICE FOR A CAPACITIVE PRIMARY ELEMENT

[75] Inventor: Erhard Lehle, Muehlheim, Fed. Rep. of Germany

[73] Assignee: Honeywell GmbH, Fed. Rep. of Germany

[21] Appl. No.: 531,972

[22] Filed: Sep. 14, 1983

[30] Foreign Application Priority Data

Oct. 18, 1982 [DE] Fed. Rep. of Germany ....... 3238507

[51] Int. Cl.$^4$ ............................................ G01R 27/26
[52] U.S. Cl. .................................. 324/61 R; 307/491; 307/271
[58] Field of Search ............ 324/DIG. 1, 61 R, 60 R, 324/60 CD; 307/491, 494, 271; 328/4; 73/336.5; 331/111

[56] References Cited

U.S. PATENT DOCUMENTS

| | | | |
|---|---|---|---|
| 3,546,612 | 12/1970 | Day | 328/4 X |
| 4,093,915 | 6/1978 | Briefer | 324/61 R X |
| 4,387,601 | 6/1983 | Azegami | 324/60 R X |

FOREIGN PATENT DOCUMENTS 0404022 10/1973 U.S.S.R. ........................... 324/61 R

OTHER PUBLICATIONS

Valvo Report 790423, Technische Informationen fur die Industrie, 11 pages.

*Primary Examiner*—Stanley T. Krawczewicz
*Assistant Examiner*—Jack B. Harvey
*Attorney, Agent, or Firm*—Trevor B. Joike

[57] ABSTRACT

A humidity sensor operates with a capacitive sensor element ($C_S$) which is arranged in one branch of a free-running multivibrator (MV), whereas a reference capacitor ($C_{ref}$) is arranged in the other branch of said multivibrator. Both output signals (U1, U2) of said multivibrator (MV) are averaged by means of RC elements (R3, C1; R4, C2) and supplied to a differential amplifier (DV), the output signal (Ua) of which changes the operating voltage ($U_B$) of the multivibrator (MV), and therefore, linearizes the characteristic of the capacitive sensor element ($C_S$).

4 Claims, 1 Drawing Figure

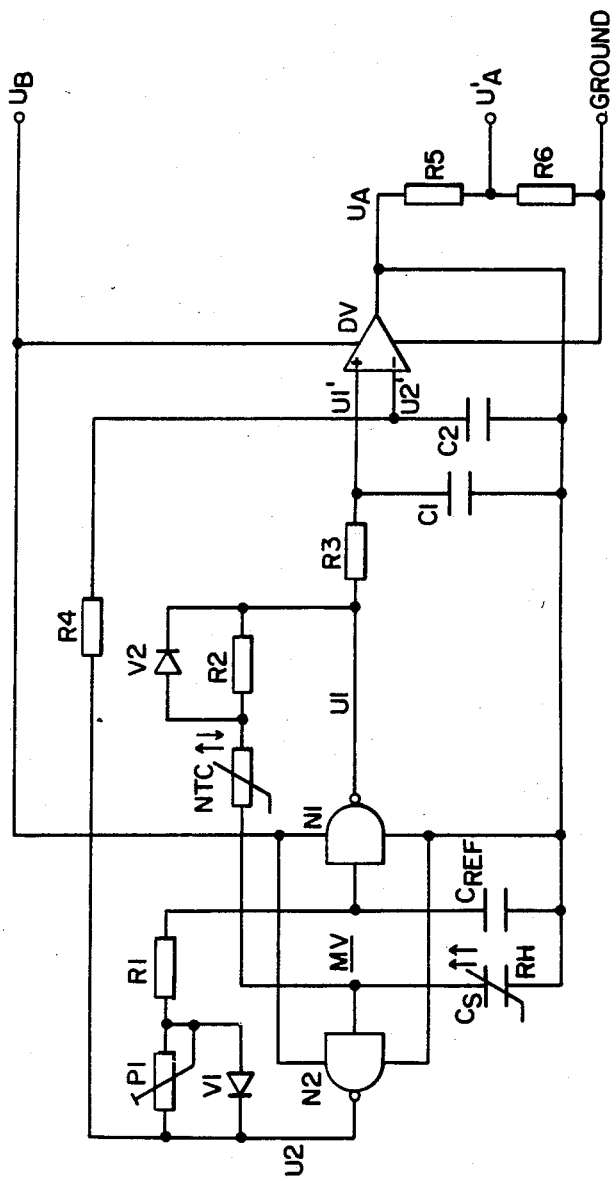

MEASURING AND LINEARIZING CIRCUIT DEVICE FOR A CAPACITIVE PRIMARY ELEMENT

BACKGROUND OF THE INVENTION

The present invention relates to a circuit device according to the preamble of claim 1.

A circuit device of this general type is known from Valvo Report 79 04 23, "Technische Informationen fur die Industrie." The basic circuit shown and described there uses two multivibrators, wherein the durations of the square-wave pulses of one multivibrator are proportional to the capacity of a reference capacitor. Those square-wave pulses are used to synchronize the square-wave oscillations of the second multivibrator, the pulse duration of which is proportional to the capacity of the measuring sensor. The output signals of both multivibrators are connected in opposition so that a resulting pulse duration is achieved which corresponds to the difference between the pulse durations of both multivibrators.

SUMMARY OF THE INVENTION

While measurement inaccuracies may arise if, during changing temperatures, both multivibrators do not exhibit the same behavior, the measured value also depends on the operating voltage. Therefore, that operating voltage must be stabilized. For compensation of the non-linear characteristic of the capacitive measuring sensor, a circuit comprising an RC element is used, which circuit on the one hand is supplied via a diode from the measuring voltage and on the other hand is supplied via a resistor from the operating voltage.

It is therefore the object of the present invention to increase measuring accuracy and to reduce complexity of the circuit device with respect to the known circuit device. The solution of said object is achieved according to the circuit device as claimed in claim 1. Further advantageous embodiments of the circuit device according to the invention may be taken from the subclaims.

BRIEF DESCRIPTION OF THE DRAWING

The circuit device according to the invention shall be further described with respect to the single FIGURE of the attached drawing.

DETAILED DESCRIPTION

A free-running multivibrator MV consists of two CMOS-NAND components N1 and N2 which are symmetrically wired up. A reference circuit consists of a calibration potentiometer P1 which is connected in series to a resistor R1 and to a reference capacitor $C_{ref}$. Further, a diode V1 is connected in parallel to the calibration potentiometer P1. A measuring circuit consists of a resistor R2 to which a resistor NTC having a negative temperature coefficient and a measuring capacitor $C_S$ are connected in series. Furthermore, a diode V2 is connected in parallel to the resistor R2. The measuring capacitor $C_S$ for instance is a capacitive humidity sensor which has a non-linear characteristic. The reference circuit and the measuring circuit both form the cross-coupled branches of the free-running multivibrator MV. Both output signals U1 and U2 of the multivibrator MV are connected via average value forming RC elements to the highly resistive inputs of a differential amplifier DV having a high in phase suppression. The RC elements consist of resistors R3 and R4, respectively, and capacitors C1 and C2, respectively. The difference between the average input voltages U1' and U2' appears as output voltage Ua at the output of the differential amplifier by the gain of said amplifier. This output voltage on one hand is connected to ground via the series connection of two resistors R5 and R6, wherein the actual output voltage U'a is picked off from the voltage divider formed in this way.

The output Ua of the differential amplifier DV serves as one terminal of the operating voltage $U_B$ which feeds the free-running multivibrator MV. The linearizing action results as follows: If for instance the relative humidity increases, then the capacity of the capacitive humidity sensor also increases and the output voltage Ua of the differential amplifier DV becomes more positive. Therefore, the operating voltage of the multivibrator decreases since its negative supply voltage is given by the output voltage Ua of the differential amplifier. However, with a decreasing operating voltage of the multivibrator the sensitivity $(U1-U2)/\Delta C_S$ also decreases. Therefore, the progressive characteristic of the sensor is linearized by the declining characteristic of the transducer's circuit. By means of the gain factor of the differential amplifier DV, which may be empirically evaluated, an optimum linearity may be adjusted.

The functional relationship of temperature with respect to the humidity sensor between 10° C. and 20° C. is higher than between 20° C. and 30° C. The resistor NTC having a negative temperature coefficient is matched to said non-linear temperature characteristic, and therefore, compensates the functional relationship of temperature with respect to the measured value.

The embodiments of the invention in which an exclusive property or right is claimed are defined as follows:

1. A circuit arrangement for linearizing a capacitive measuring sensor comprising:
   a capacitive measuring sensor;
   a reference capacitor;
   multivibrator means having first and second switching means, first cross coupling means including said reference capacitor for connecting an output of said second switching means to an input of said first switching means, and second cross coupling means including said capacitive measuring sensor for connecting an output of said first switching means to an input of said second switching means; and,
   difference sensing means having a first input connected to the output of said first switching means and a second input connected to an output of said second switching means, said difference means providing an output which is an average of output signals from said first and second switching means of said multivibrator means.

2. The arrangement of claim 1 wherein said first cross coupling means includes a calibration resistor connected in series with said reference capacitor.

3. The arrangement of claim 1 wherein said second cross coupling means includes a negative temperature coefficient resistor connected in series with said capacitive measuring sensor.

4. The arrangement according to claims 1, 2 or 3 wherein said difference sensing means comprises a differential amplifier having first and second inputs and an output and further comprises a first RC network for connecting the output of said first switching means to said first input of said differential amplifier and a second RC network for connecting the output of said second switching means to said second input of said differential amplifier, wherein said output of said differential amplifier serves as one of two terminals for supplying operating voltage to said multivibrator means.

* * * * *